United States Patent [19]

Hasslinger

[11] 4,149,540
[45] Apr. 17, 1979

[54] SEPARABLE CINCH FASTENER

[75] Inventor: Russell Hasslinger, Wyckoff, N.J.

[73] Assignee: Velcro USA Inc., New York, N.Y.

[21] Appl. No.: 715,510

[22] Filed: Aug. 18, 1976

Related U.S. Application Data

[63] Continuation-in-part of Ser. No. 592,600, Jul. 2, 1975, abandoned.

[51] Int. Cl.² ............................................. A61B 17/12
[52] U.S. Cl. .................................. 128/327; 24/16 R; 128/DIG. 15
[58] Field of Search ................... 24/16 R, 17 A, 17 B, 24/204; 128/327, DIG. 15

[56] References Cited

U.S. PATENT DOCUMENTS

| 721,162 | 2/1903 | Denain | 128/327 |
|---|---|---|---|
| 2,113,534 | 4/1938 | Brown | 128/327 |
| 2,693,794 | 11/1954 | Neville | 128/327 X |
| 3,063,718 | 11/1962 | Steinkamp | 128/DIG. 15 |
| 3,086,529 | 4/1963 | Munz et al. | 128/327 |
| 3,426,363 | 2/1969 | Girard | 2/338 |
| 3,535,718 | 10/1970 | Murcott | 128/133 X |
| 3,586,001 | 6/1971 | Sanderson | 128/327 |
| 3,603,316 | 9/1971 | Lehman | 2/338 X |
| 3,631,568 | 1/1972 | Wolfe et al. | 24/16 R |
| 3,640,273 | 2/1972 | Ray | 128/133 X |
| 3,845,769 | 11/1974 | Shaw | 128/DIG. 15 X |
| 3,947,927 | 4/1976 | Rosenthal | 128/DIG. 15 |

Primary Examiner—Robert W. Michell
Assistant Examiner—Michael H. Thaler

Attorney, Agent, or Firm—Pennie & Edmonds

[57] ABSTRACT

A separable fastening device is disclosed which is adapted to encompass at least one member in gripped relation and to facilitate the simultaneous application of cinching and fastening forces which place the fastener in tension and are uniquely retained in the fastening device. The fastening device has a first flexible strap having on one surface a plurality of upstanding hook and loop-type engaging elements, a second strap having on a surface opposite the first surface, a plurality of mating upstanding hook and loop-type engaging elements, with means being provided to connect the first and second straps, and retaining means connected to the free end of the first strap, the retaining means defining an opening configured to receive the free end of the second strap. The opposed positions of the mating engaging elements are such that when the fastening device is positioned about the member with the free end of the second strap extended through the retaining means, at least retaining the retaining means in a fixed position and applying cinching forces to the free end of the second strap, causes the device to grip the member, and simultaneously pressing the surfaces of mating engaging elements in face-to-face relation provides face-to-face engagement of the strap portions to retain the grip thereby applied. In the preferred embodiment the separable fastening device comprises a tourniquet utilizing a retaining means either in the form of a pull-ring or a relatively short retaining strap to retain one end of the fastening strap while the other end is cinched.

28 Claims, 9 Drawing Figures

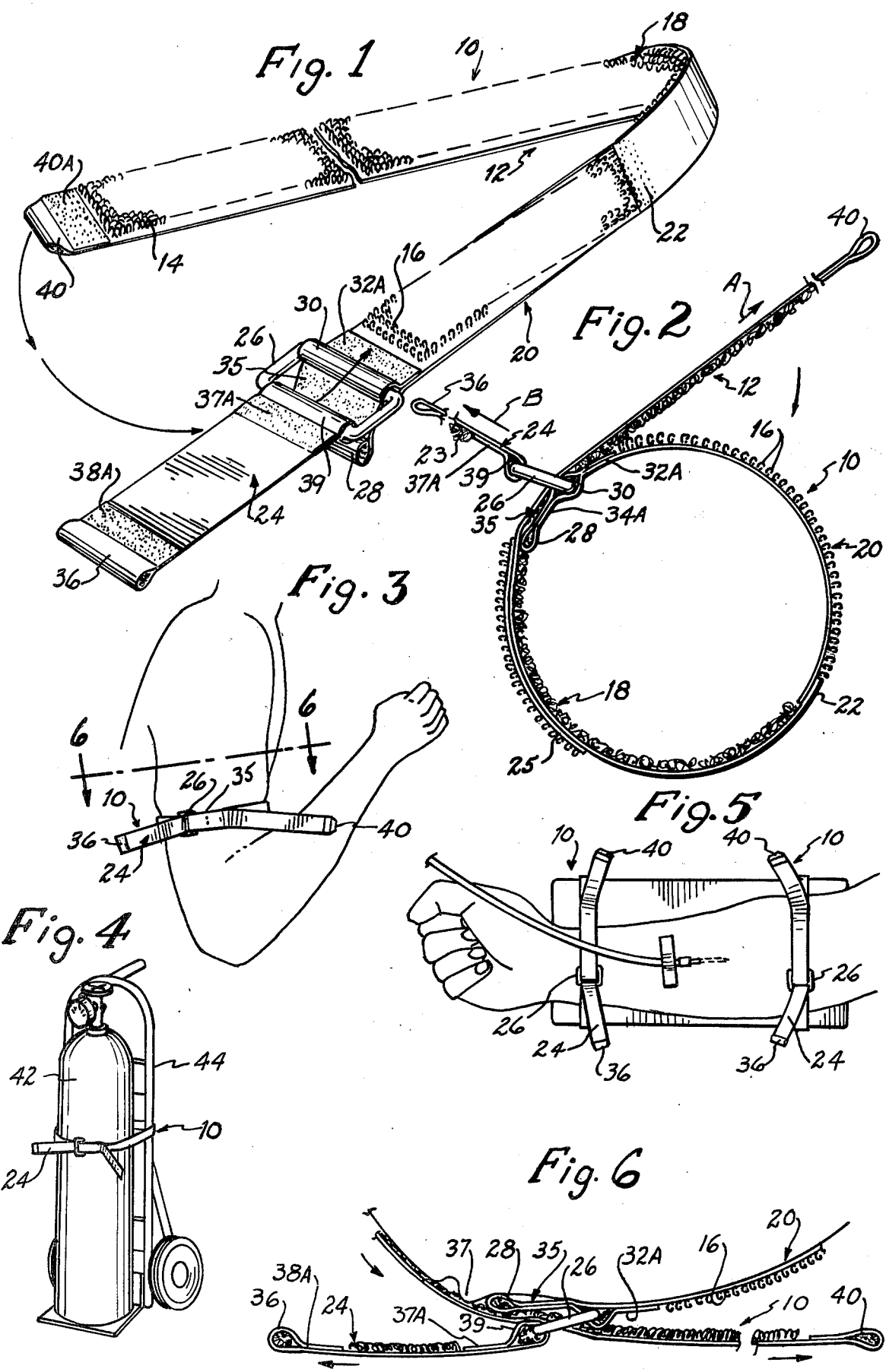

Since in another preferred form the retaining means is in the form of a retaining strap connected to a genrally endless ringlike member, it has been found that in the adaptation of the strap for use as a tourniquet, the generally endless connecting ring produces pinching forces on surface portions of the skin of the limb which are contiguous to the ring-like member when the strap is tightly gripped about the limb. Thus, in this embodiment of the invention it has also been found to be particularly advantageous to provide a relatively short strap portion connected to the main strap portion at the endless ring connection, This short strap portion if configured and dimensioned to extend across the ring opening to provide a protective barrier for the skin.

The free end portion of the short strap is arcuately configured by folding it upon itself and securing it thereto preferably by ultrasonic welding. This arcuate configuration is provided to smooth excessive skin portions of the human limb as the tourniquet is cinched thereabout thereby providing a significant anti-pinch feature by accumulating the excessive skin forward of the short strap and away from the ring-like member.

It will be seen further that in the tourniquet embodiment of the invention, although he hook and loop-type fastener sections permit adjustability to the size of the strap, the strap may also be provided in several sizes so as to accomodate human limbs of various sizes and take into consideration the size variations between arms and legs and the individual body size variations between patients.

Further, it will be seen that although the preferred embodiment of the invention relates to the provision of a blood constriction device for parts of the human body such as arms, legs, etc., in its broadest sense the inventive concept may be utilized to secure any device to any member by connecting a first strap portion configured as one end of the inventive fastening device to a first part of the device to be secured and a second strap portion confirgured as the other end of the inventive fastening device to another part of the device to be secured. This arrangement will utilize the inventive fastening embodiment herein in a similar manner as is utilized in the inventive tourniquet. For example, preformed casts for human limbs and the like may be secured therearound with the inventive strap arrangement. Alternately, structural devices and the like may be secured about any member quite readily by attaching the strap portions disclosed herein to opposed end portions of the member to be secured.

BRIEF DESCRIPTION OF THE DRAWINGS

Preferred embodiments of the invention are decribed hereinbelow with reference to the drawings wherein:

FIG. 1 is a presepctive view of the cinch fastener strap assembly of the present invention;

FIG. 2 is a side view of the cich fastener strap assembly of FIG. 1 illustrating the preferred cicnching technique utilized to tightly grip a member therewithin;

FIG. 3 is a side view of a human arm illustrating the use of the cinch fastener strap assembly as a tourniquet;

FIG. 4 is an illustration of an alternate use of the cinch fastener strap assembly ro secure an oxygen tank to a handcart;

FIG. 5 is a view of an illustration of an application of two cinch fastener strap assemblies of the invention to releasably secure a limb of a human being to an intraveneous (I.V.) board;

FIG. 6 is a view taken along lines 6—6 of FIG. 3;

DETAILED DESCRIPTION OF THE PREFERRED EMBODIMENTS

Figure 7:
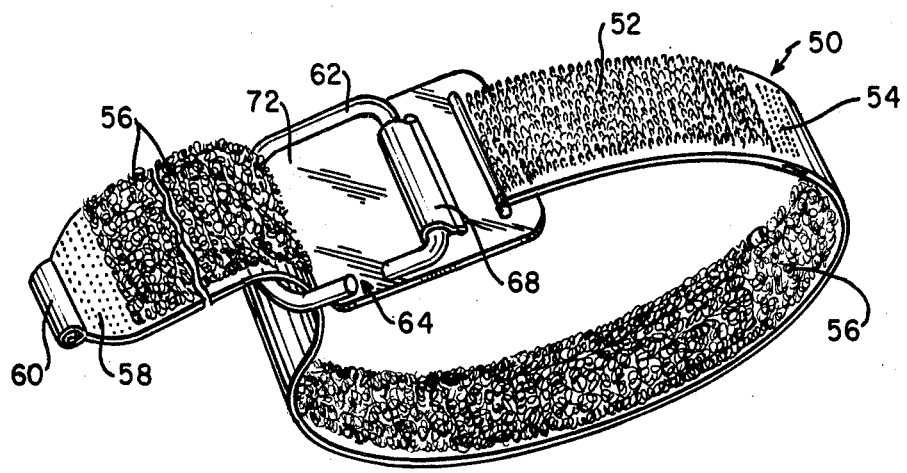
FIG. 7 is a perspective view of an alternate preferred embodiment of the cinch fastener strap of the invention.

Referring initially to FIG. 1 there is illustrated a fastener 10 in the form of a cinch strap assembly. The strap assembly is comprised of a main flexible strap section 12 which has on a first section 18, a surface portion having a plurality of upstanding loop-type engaging elements 14, and on an opposite surface portion of a section 20 adjacent the first section, mating hook-type engaging elements 16 upstanding therefrom and facing a direction opposite the direction of elements 14. The main flexible strap section 12 may be entirely integrally constructed, or it may be sectioned and attached to a separate device to be secured as will be described later in connection with FIG. 9. In its preferred form, the srap is constructed of a first length of VELCRO ® brand loop fastener tape 18 connected at 22 to a second length of VELCRO ® brand hook fastener tape 20 such that the loops 14 of the first tape section 18 and the hooks 16 of the second tape section 20 face in opposite directions.

Since VELCRO ® brand fastener tapes are generally constructed of a synthetic material, such as nylon, which softens under the action of heat or ultrasonic energy, it has been found that these fastener tapes are best assembled by ultrasonically welding the sections together at 22 as shown in FIG. 1. However, other known securing techniques such as sewing, gluing, etc., are also comtemplated.

A retaining strap 24 is secured to the main strap assembly at one end as shown in FIG. 1, by a generally endless metallic ring 26 — which is preferably of stainless steel. The ring 26 is secured to an end portion of the main strap by laying the strap on a flat surface, placing the ring in position against the hook surface over backwardly through the ring to form an arcuate loop-like end portion 28 and a short strap extension 35 as illustrated in the drawings. The tape portions at 32A and 34A are then ultrasonically welded together. Since the folded tape portion includes hook surfaces which are folded in face-to-face relation, the ultrasonic welding, or other securing technique will actually secure the surfaces of hooking elements together in face-to-face relation at 32A and 34A.

In a similar manner the end portions of the retaining strap 24 are folded upon themslves and ultrasonically welded in position at 37A and 38A, leaving end loops 36 and 39 as shown. The free end portion of the main strap is also folded upon itself and secured as shown at 40A to form a loop-like gripping end 40 in FIG. 1. Although cinching forces may be applied to retaining strap 24, this strap is intended primarily to provide retaining forces to one end of the main strap by gripping it and at least holding it in a fixed position while cinching forces are applied to the main strap assembly 12.

Referring now to FIG. 2, the fasteneing device of FIG. 1 is placed in encircling relation about one member, or it may be placed in emcompassing relation with two or more members (not shown). The member may be cylindrical, or it may have any cross sectional shape which is suitably encircled by the flexible strap 10, or it may have a uniform or varying cross section along its length. It should be noted that the specific configuration or relative flexibility or rigidity of the member to be gripped does not affect the gripping capability of the fastening device, since the cinch strap assembly is not only flexible and resilient, but uniquely structured to facilitate the application of the cinch forces to members of any configuration or shape. It can be seen further that the loop-like end portions 36 and 40, combined with the arrangement of hook and loop tapes as shown, provide convenient gripping means which make it possible to apply the improved cinching forces about the member - whether it is flexible or rigid - and to retain these cinching forces without loss of tension forces in the strap.

Although in the preferred embodiments illustrated in the drawings, the retaining strap 24 is illustrated as a separatable fastener tape, it should be understood that any strap may be used as a retainer strap provided it is of sufficient strength to withstand the forces applied. However, the use of a loop fastener tape as shown in FIG. 2 has the advantage in that it may be stored by securing it to section 18 of the main strap portion 12 after cinching by pressing it against hook tape 25 which is secured to the reverse side base member of the tape section 18 as shown.

In FIG. 3, the fastener strap assembly 10 of FIGS. 1 and 2 is illustrated for use as a tourniquet to constrict or control the blood flow through a human arm by encircling the portion of the arm as shown. For the purposes of illustration, the tourniquet is shown with the ring 26 positioned adjacent the side of the limb muscle. However, in practice, the ring is generally positioned at the forward portion of the limb - i.e. 90° from the position shown - so as to provide contacting relation between the strap portions and the side and lowr portions of the limb. The free end portion 40 of the main strap is then threaded through the endless ring 26. One end portion of the main strap is maintained in fixed position by gripping and retaining strap 24 while cinching forces are applied to the main strap assembly by gripping and forcing end portion 40 in the direction illustrated by arrow "A" in FIG. 2. Strap 24 is gripped and retained by gripping arcuate end portion 36. Strap 24 may either be held in a fixed position to merely oppose the forces on end portion 40 of the main strap 12, or alternately, cinching forces may be applied to retaining strap 24 along the general direction illustrated by arrow "B". By simultaneously placing the engaging elements of the VELCRO® brand fastener members in face-to-face relation while applying the requisite cinching forces to the gripping ends. 36 and 40 respectively, the grip created by the fastener about the arm is progressively and simultaneously applied and maintained by a single fastening action. The simultaneous pressing and cinching technique is particularly made possible by the relative resilient flexibility of the engaging elements upstanding from opposed surfaces wherein in practice, portions of the hook elements of one surface are resiliently flexed while the loop elements of the other surface are pressed thereagainst while simultaneously being shifted longitudinally thereacross by the cinching forces. Therefore, it will be seen that prior to achieving full surface-to-surface engagement of the fastening surface of the members, some relative shifting and rubbing of the mating surfaces may take place as a result of the cinching forces along the interfacial plane therebetween while they are substantially in face-to-face relation and some hooking elements may actually be resiliently forced past each other. However, once the fastener materials are fully engaged they will be separable by peeling forces normal to the interfacial plane of engagement but will resist forces in a plane substantially parallel to the interfacial plane of engagement.

Referring once again to FIG. 3, when the fastener is used as a tourniquet, the relatively short starp portion 35 functions as a unique anti-pinch device by protecting the skin of the human limb from being "pinched" upwardly into the opening of the ring 26 as the main strap 18 is tightened about the limb. Short strap 35 blocks the opening of the ring 26 and provides a protective barrier between the skin of the arm and the ring 26.

In addition to providing a physical barrier between the opening of ring 26 and the adjacent skin portion of the limb, the short strap 35 is arcuately configured at its free end portion to form a looped end 28 which smooths over excessive skin portions as the main strap 18 is tightened about the limb. Thus, referring to FIG. 6, when the main strap 18 is tightened, the short strap 35 is in contiguous relation with the skin and as the strap section 12 moves in the direction of arrow "A", the loop-like end portion 28 of the short strap 35 smooths the excess skin and causes an accumulation 37 thereof immediately forward of the loop-end 28. While this accumulation of skin will somewhat approach a "pinch" condition, it nevertheless is preferred to the pinched skin condition which would otherwise occur without the short strap 28. Thus, the strap 28 may be appropriately referred to as an "antipinch skin roll protector".

In practice, when the inventive strap is adapted for use as a tourniquet, it has been found advantageous to merely grip and retain retaining strap 24 in a stable fixed position - or to apply forces primarily in a direction away from the limb surface - while applying cinching forces only to the end portion 40 of the main strap 12. This procedure lifts the endless ring member 26 away from the skin and minimizes discomfort to the patient, while permitting the accumulation, or "rolling" of excessive skin portions by the looped end as previously described. Alternatively, cinching forces may be applied to the retaining strap 24, in addition to the lifting forces directed away from the limb with the resultant force vector being in the direction illustrated by arrow "B" in FIG. 2.

FIG. 4 illustrates the use of the cinch strap to secure an oxygen tank 42 to a handcart 44. It will be seen that to secure rigid members of varying dimensions and uneven shapes together it was generally difficult with prior art straps to provide sufficient cinching forces substantially simultaneously with fastening forces to achieve the precise degree of strap tension required without any loss of the grip. This was particularly the case when rigid members were strapped together because of the absence of resilience or flexibility in the members. Also, with prior art locking devices such as buckles, clasps, etc., precise fastening was not possible. The present cinch strap assembly makes it possible to apply and retain such cinching forces and this advantage is considered as a significant feature of the present invention.

Referring now to FIG. 5, two straps 10 constructed in accordance with the invention are used to secure an intraveneous (I.V.) board to the arm of a patient. It can be seen in FIG. 5 that the cinch straps 10 are capable of

SEPARABLE CINCH FASTENER

CROSS-REFERENCE TO RELATED APPLICATIONS

This application is a Continuation-In-Part of my co-pending U.S. Patent application Ser. No. 592,600, filed July 2, 1975, now abandoned.

BACKGROUND OF THE INVENTION

1. Field of the Invention

This invention relates to a separable fastener which is in the form of a cinch strap.

2. Description of the Prior Art

Separable fasteners such as those described in U.S. Pat. Nos. 2,717,437 and 3,009,235 which are marketed under the registered trademark VELCRO brand hook and loop fasteners by Velcro Corporation, 681 Fifth Avenue, New York, N.Y. have gained wide acceptance because of the properties of the mating hooks and loops which permit their attachment by merely placing a surface defined by the hooks into face-to-face relationship with a surface defined by the loops so that a large number of hooks engage a large number of loops which resist separation parallel to the interfacial plane of engagement but are readily separable by peeling forces applied substantially normal to this interfacial plane. These fastening devices are generally formed of a sheet of synthetic woven or knitted fabric having raised threads of synthetic material, such as nylon, which are napped or unnapped to provide a pile surface defined by a plurality of loops, and which may be thermally treated to become semi-rigid. Certain of the loops may then be cut along one side near their outer extremity to form hooks.

These fasteners have been utilized in numerous applications in many fields of use, particularly because of their unique touch and close fastener capability as well as their fastening strength. The patents which have issued are legion in which the unique fastening capability of these hook loop-type engaging elements have been applied to particular uses to create new and unobvious fastener arrangements.

One field of use in which these fasteners have been utilized in the past pertains to straps of several types. Although the prior art dealing with straps and the like includes numerous other fastener devices to secure the straps in their intended environment, the applications of these separable hook and loop-type fasteners have in many respects, eliminated the need for the traditional strap fastening devices such as buckles and the like. To the extent that the early fastening devices did not generally facilitate variable and precise fastening, the application of these separable fasteners to the strap art has proven to provide substantial advantages.

U.S. Pat. No. 721,162 to Denain relates to a hemostatic bandage of a relatively complex and expensive construction and which utilizes a relatively complex buckle for fastening the device in position. U.S. Pat. No. 2,514,796 to Rishcoff relates to a support belt which incorporates a relatively complex device for securing it in position. U.S. Pat. No. 2,815,752 to Forman relates to a circular adhesive bandage. U.S. Pat. No. 3,535,718 to Murcott relates to a restraint device for mounting upon wrist and ankles and utilizes coupling members to secure the device in position. U.S. Pat. No. 3,603,316 to Lehman relates to an abdominal belt having an elastic portion and elastic draw strips. U.S. Pat. No. 1,473,041 to Henderson relates to a Tourniquet having an interior integral surface bar for conveying localized pressure. U.S. Pat. No. 3,000,384 to Piers, Jr. relates to a Fastener Tie to retain a bank or lock of hair in a desired design or arrangement. In one embodiment, portions of the tape are longitudinally elastic. U.S. Pat. No. 3,086,529 to Munz et al. relates to Constrictors comprising a length of elastomer adapted to be stretched about a human limb with VELCRO brand fastener tapes adapted to secure the constrictor in position. U.S. Pat. No. 3,190,444 to Kelson relates to Rotating Tourniquets which are placed about three of a patient's limbs and rotated periodically from limb to limb. U.S. Pat. No. 3,586,001 to Sanderson relates to a Medical Compress which utilizes VELCRO ® brand fasteners in combination with a cushion to constrict the flow of blood in a limb of a wearer. U.S. Pat. No. 3,827,107 to Moore relates to an Adjustable Strap Assembly which utilizes VELCRO ® brand fasteners in combination with a pad having hooking elements on both sides to eliminate the requirement for an excessively long length of looped strap portion. Other prior art patents include:

U.S. Pat. No. 2,519,712 to Stegeman
U.S. Pat. No. 3,279,459 to Schenker
U.S. Pat. No. 3,430,299 to Copen
U.S. Pat. No. 3,372,438 to Rinecker
U.S. Pat. No. 3,376,865 to Gamper
U.S. Pat. No. 3,390,680 to Marcum
U.S. Pat. No. 3,416,516 to Cohen et al.
U.S. Pat. No. 3,467,077 to Cohen
U.S. Pat. No. 3,570,495 to Wright
U.S. Pat. No. 3,633,567 to Sarnoff
U.S. Pat. No. 3,669,096 to Hurwitz
U.S. Pat. No. 3,880,161 to Fossell In the prior art applications of VELCRO ® brand fasteners to straps and the like, the structure has always been adapted such that the hook and loop-type fasteners are secured by a touch and close action. None of these patents disclose a cinch fastener which is so constructed and arranged to facilitate fastening the hook and loop-type fastener materials with multidirectional opposed cinching forces with a single movement in which the gripping tension forces as well as the retention of said forces is accomplished without loss of grip.

SUMMARY OF THE INVENTION

The present invention relates to a separable fastening device adapted to encompass at least one member in gripped relation which comprises a first flexible strap portion having on a first surface portion a plurality of engaging elements upstanding therefrom and a second strap portion having on a surface portion opposite said first surface portion a plurality of mating engaging elements upstanding therefrom. The invention further comprises means to connect the first and second strap portions and retaining means connected to the free end portion of said first strap portion, the retaining means defining an opening configured to receive the free end portion of the second strap portion. The opposed positions of the mating engaging elements are such that when the device is positioned about the member with the free end portion of the second strap portion extending through the retaining means, at least retaining the retaining means in a substantially fixed position and applying cinching forces to the free end portion of the second strap portion will cause the device to grip at least a portion of the member, and substantially simultaneously pressing the surfaces of mating engaging elements in face-to-face relation provides face-to-face engagement of the strap portions to retain the grip thereby applied.

The preferred embodiment of the invention in one of its broadest forms relates to a separable fastening device adapted to encompass at least one member in gripped relation which comprises a cinch strap including a main flexible strap portion having on one surface portion a plurality of resilient engaging elements upstanding therefrom and on an opposite surface of a strap portion adjacent thereto, a plurality of mating engaging elements upstanding therefrom, retaining means being connected to the main strap portion at one end portion thereof and the other being free. The retaining means defines an opening configured to receive the free end portion of the main strap portion while the adjacent opposed positions of the mating engaging elements are such that when the main strap portion is positioned about the member with the free end portion extending through the retaining means, at least retaining the retaining means in a substantially fixed position and applying cinching face to the free end portion of the main strap portion will cause the strap to grip at least a portion of the member and substantially simultaneously pressing the surfaces of the mating engaging elements in face-to-face relation provides face-to-face engagement of the strap portions to retain the grip thereby applied.

Although one preferred embodiment of the fastening device of the invention utilizes a ring-like member to transmit retaining forces to a strap portion, another embodiment includes a retaining strap connected to a main strap portion to provide transmission of cinching forces thereto. This particular embodiment is also in the form of a separable fastening device comprising a cinch strap assembly adapted to encompass at least one member in gripped relation and to provide simultaneous cinching and fastening forces which substantially maximize the grip while uniquely retaining the forces applied to the strap. This fastener device comprises a cinch strap assembly which includes a main flexible strap portion having on one surface portion a plurality of resilient engaging elements upstanding therefrom, and on an opposite surface of a strap portion adjacent thereto, a plurality of resilient mating engaging elements upstanding therefrom. The invention further comprises a retaining strap which, in a preferred embodiment, is of sufficient length to provide convenient gripping thereof, and which is preferably configured at an end portion to facilitate gripping thereof. The retaining strap is connected to the main strap portion at one end portion and the other end portion of the main strap portion is free. The strap further comprises means to connect the retaining strap to the main strap portion . The connecting means in this embodiment defines an opening configured to receive the opposite — or free end — portion of the main strap when it is wrapped in encompassing relation with the member to be gripped. The mating engaging elements on each mating surface portion of the main strap portion are so arranged that when the strap is positioned about the member to be gripped, with the free end portion extended through the opening of the connecting means, at least retaining the retaining strap in a substantially fixed position, while applying cinching forces to the free end portion of the main strap causes the strap to grip at least a portion of the member while substantially simultaneously pressing the surfaces of resilient mating engaging elements in face-to-face a relation provides face-to-face engagement of these strap portions. This mating engagement is relatively resistant to forces parallel to, or within the plane of engagement, but the surfaces are readily separable by peeling forces normal to the interfacial plane of engagement. This fastening capability retains the strap portions in face-to-face relation to retain the grip thereby applied to the member.

Although the cinch fastener strap may be of a unitary construction, preferably it is constructed of VEL-CRO ® brand separable fastener tape materials suitably secured to each other to provide the desired arrangement. These separable fasteners to which I refer have a base member, woven or knitted of a synthetic heat deformable material such as nylon, and have resilient engaging elements uptanding from the respective base member. In the preferred embodiment the engaging elements are constructed in the form of hook-like elements which mate with looplike hooking elements on the opposed engaging surface portions. However, it should be understood that any flexible engaging elements, including mushroom-like elements, resilient projections, etc., which are readily securable in face-to-face relation, and which particularly resist forces parallel to the interfacial plane of engagement, are comtemplated within the scope of the present invention, provided the fastener strap is flexible. Such mushroom configured hooking elements as the type disclosed in U.S. Pat. Nos. 3,138,841 and 3,320,649, both of Naimer, and U.S. Pat. Nos. 3,718,725 and 3,770,359, both to Hamano are contemplated. Futther examples of knitted form fastener members contemplated within the scope of the present invention are disclosed in U.S. Pat. Nos. 3,530,687 and 3,539,436, both to Hamano.

In a preferred embodiment the cinch fastener of the invention is constructed particularly for use as a tourniquet to constrict or control the flow of blood through the limb of a human being. Although the main srap portion need not beelastic, it has been found advantageous to construct such a tourniquet as a cinch fastener having strap portions in which the base material is constructed of a woven or knitted yarn and incorporates elastic filamentary yarns which provide elastic retention forces to constrict the flow of blood in the limb. The advantages of an elastic strap are particularly apparent when combined with the unique cinching and fastening capability of the invention, Also, the "knitted base" embodiment is particularly useful for use as a blood flow control device, because the mechanical elasticity of the knitted base material provides sufficient elastic restraint to the cinch fastener strap. Further, when the knitted base material is constructed at least in part, of an elastic yarn material, the resultant elastic properties exhibited by the cinch fastener strap are due to both the inherent mechanical elasticity of the knitted construction, as well as the basic elasticity of the elatic yarn materials, both of which render the strap stretchable and elastic.

Since in its preferred form the retaining means is in the form of a generally endless pull ring defining an opening therethrough, it has been found that in the adapation of the strap for use as a tourniquet, a flat relatively short strap of plastic material may be connected to the end portion of the strap to which the pull ring is connected to provide a barrier between the pull ring and the skin of the limb which is being gripped by the tourniquet.

firmly securing the arm of a patient to the I.V. board as shown. Thus it is apparent that whether the members are two rigid members as in FIG. 4, or one rigid member and one relatively non-rigid member (as in FIG. 5), the cinch strap of the invention is capable of applying and securing the fastening forces, precisely as may be required in a given arrangement.

FIG. 7 illustrates an alternate preferred embodiment of the invention which avoids the use of the retaining strap of the previous embodiments. A cinch fastener strap 50 is comprised of a first VELCRO ® brand hook fastener tape 52 connected by an ultrasonic welded portion 54 to a second length of VELCRO ® brand loop fastener tape 56. The free end portion of the loop fastener tape 56 is folded upon itself and ultrasonically welded thereto at 58 to form a convenient gripping member 60. A pull ring 62 — which is preferably split at 64 to receive the tape section 56 — is secured to the other end portion of the hook tape section 52 and maintained in position within a portion of the tape section which is folded through the ring, looped upon itself, and ultrasonically welded at 70 to form an attachment 68. The portion of the tape section 52 which is looped upon itself is secured by an ultrasonically welded portion 70 seen clearly in FIG. 8.

Figure 8:
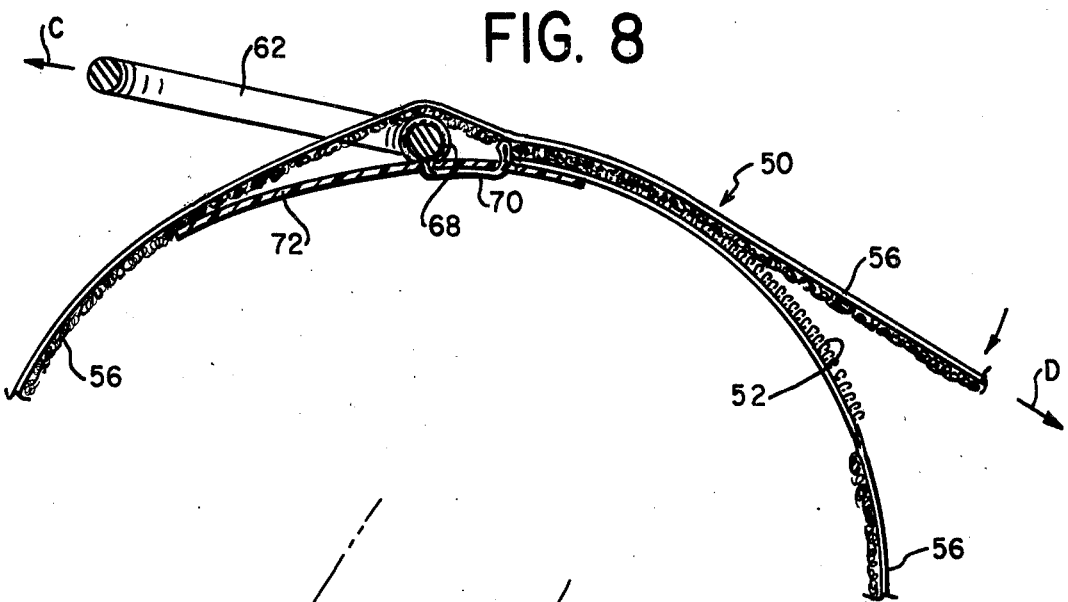
FIG. 8 is a cross-sectional view of the cinch fastener strap of FIG. 7 illustrating the preferred cinching technique utilized to tightly grip a member therewithin.

Referring further to FIG. 8, a protective barrier member 72 in the form of a relatively shorter sheet of plastic material such as polyethylene, polypropylene, nylon and the like, is attached to the end portion of the tape section 52 at the ring connection end and provides protection for the skin surface of a human limb when the fastener strap is utilized as a tourniquet and cinched therearound. FIG. 8 clearly shows the preferred application of the requisite cinch fastener forces to the cinch fastener member, which forces may conveniently be applied by gripping the ring member 62 with the thumb or forefinger and by pulling in the direction of arrow C while simultaneously gripping and pulling tape section 56 in the direction of arrow D. Thus, the retaining - or pull-ring 62 provides a convenient retaining means for the cinch fastener strap of the invention.

Figure 9:
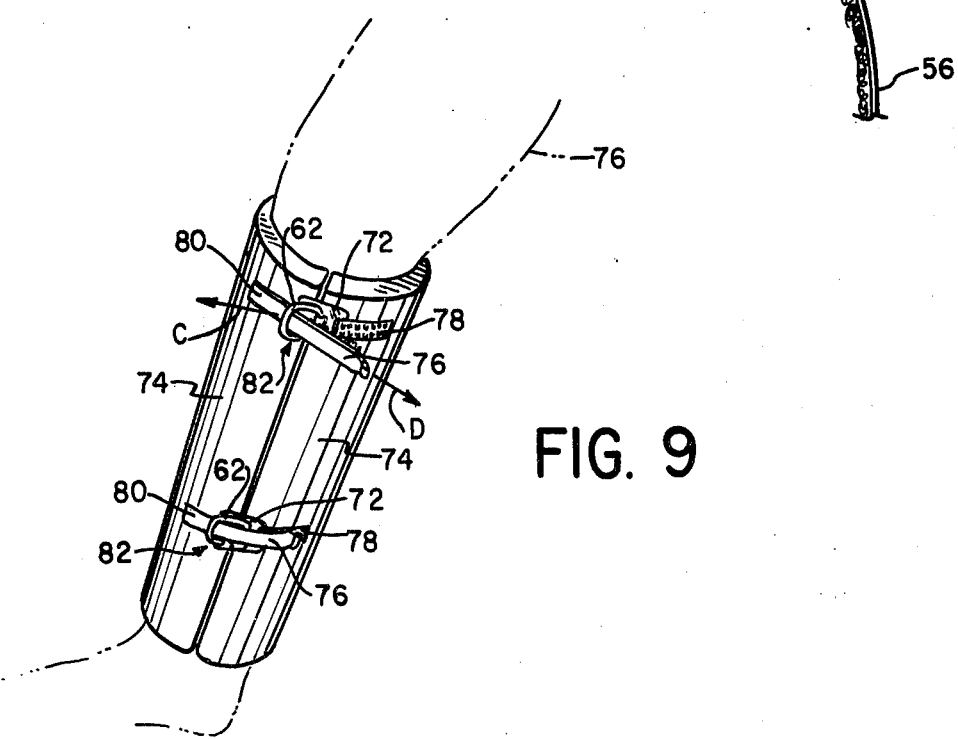
FIG. 9 is a perspective view illustrating another alternae embodiment of the cinch fastener strap of the invention.

FIG. 9 illustrates an alternate us of the invention. As can be seen in the drawing, one end portion of the inventive cinch fastener strap may be attached to a device which is to be secured and the other inventive end portion may be attached to another section of the device to be secured. For example, FIG. 9 illustrates the use of the separable cinch fastener to secure a preformed cast 74 about a human limb such as leg 76. The separable cinch fastener 76 is comprised of hook fastener tape section 78 attached to one end portion of the cast 74 and pull ring 62 attached to the hook fastener section in the same manner as illustrated in the embodiment of FIG. 7. A sheet of plastic material 64 provides a barrier between the pull ring 62 and the cast 74 and a section of VECTRO ® brand loop fastener tape 80 is attached to the other end portion of the cast. The fastener is cinched by forces directed along arrows C and D as described previously. Similarly, any number of fasteners identical to fastener 76 may be provided as is illustrated in FIG. 9 by the fastener 82.

Referring once again generally to the embodiments illustrated in the drawings, the cinch fastener may also be constructed of VELCRO brand hook and loop-type fastener straps in which the straps exhibit elastic properties in at least one direction. Such a fastener material will be provided with elastic material such as natural or synthetic rubber or rubber base yarn, generally in the warp direction so as to provide elasticity at least along the length of the fastener tape. When the cinch fastener is constructed of separable fastener tape members which are elastic at least in the longitudinal direction, its use and function as a tourniquet is particularly enhanced. The unique cinching technique illustrated in FIG. 2, combined with the stretchability of the fastener material in the direction of the arrows "A" and "B" provide residual restraining forces which act to return the material to its original dimension prior to being elongated by the cinching forces. Therefore it can be seen that the cinching forces provided by this embodiment are useful, particularly because of the resilient elongation of the cinch fastener.

In addition to the embodiments and applications illustrated, the inventive fastener may be utilized in numerous other applications, particularly due to its particular single action fastening ability. For example, the fastener is suitable for use for stretchers, gas masks, hospital beds, shoes for the handicapped, wheelchairs, traction straps, splints, spine board straps, EKG straps, arm slings, wrist and ankle restraints and rib supports, etc. While straps of other types may be used for the above applications, it has been found that the unique single action cinching fastening of the present invention makes it possible to achieve the required fastening with unusual speed while providing fastening capability previously unattainable, notwithstanding the relative flexibility, resilience, rigidity, softness or hardness of the members to be secured. Further, as can be seen from the foregoing, the scrubbing is accomplished in an improved manner notwithstanding the fact that the members to be secured have irregular nonconforming configurations.

The cinch fastener strap substantially reduces the time required to grip the member or members and, in particular, it can be seen that this time factor may be extremely significant in terms of life or death of a patient when the fastener is utilized as a tourniquet.

I claim:

1. A separable fastening device adapted to encompass at least one member in gripped relation which comprises a cinch strap including a main flexible strap portion having on one surface of a first strap section, a plurality of resilient engaging elements upstanding therefrom and on an opposite surface of a second strap section adjacent to the first strap section, a plurality of mating engaging elements upstanding therefrom such that the engaging elements of each surface of said strap sections face in opposite directions, a retaining strap connected to the main strap portion at a first end portion thereof and adapted to be gripped by hand, the second end of said main strap portion being free, relatively rigid means to connect the retaining strap to the main strap portion said connecting means including an opening configured to receive the free end portion of the main strap portion, a barrier member connected to the first end portion of said main strap portion and dimensioned to extend across at least a portion of said opening, the adjacent opposed mating engaging elements of said strap sections being positioned relative to each other such that when the main strap portion is positioned about the member with the free end portion extending through the opening of said retaining means and the engaging elements of the opposed surfaces placed in face-to-face relation, at least retaining said retaining means in a substantially fixed position while applying cinching forces to the free end portion of said main strap portion, will cause the cinch strap to grip the member while substantially simultaneously pressing the surfaces of mating engaging elements of the opposed surfaces together will provide progressively increasing face-to-face engagement of the strap portions to retain the grip thereby applied by said main strap portion, and said barrier member provides a separative layer between the opening of said retaining means and the gripped member.

2. The separable fastening device according to claim 1 wherein said main flexible strap portion comprises at least one of a woven and knitted base material and said engaging elements comprise resilient hook and loop-type engaging elements.

3. The separable fastening device according to claim 2 wherein said base material comprises at least one of a woven and knitted nylon material.

4. The separable fastening device according to claim 3 wherein said resilient engaging elements are in the form of resilient hook-type hooking elements upstanding from one surface portion of the main strap and the mating engaging elements are in the form of resilient loop-type hooking elements upstanding from the opposite surface portion of said main strap.

5. The separable fastening device according to claim 4 wherein said main strap portion further comprises a first section of separable fastener material which has hook-type hooking elements upstanding from one surface and a second section of separable fastener material secured to an end portion of said first section and having upstanding loop-type hooking elements which mate with the hook-type hooking elements of the first section, said strap sections being connected in reversed relation such that the hook-type elements of the first strap section and the loop-type elements of the second strap section face in opposite directions.

6. The separable fastening device according to claim 5 wherein said connecting means comprises a ring-like member connected to an end portion of said main strap portion and defining an opening configured to receive the opposite end portion of said main strap portion when said main strap portion is positioned in gripped relation with the member.

7. The separable fastening device according to claim 6 wherein said retaining strap is in the form of at least one of hook and loop-type fastening tape having one end connected to said ring-like member and having its free end portion folded upon itself and secured thereto to provide means to grip the retaining strap while applying cinching forces at least to the main strap portion.

8. The separable fastening device according to claim 7 wherein portions of said strap sections are positioned in overlapping relation.

9. The separable fastening device according to claim 8 wherein said strap sections are connected together by an ultrasonic welded portion.

10. The separable fastening device according to claim 5 wherein said connecting means comprises a generally endless member connected to an end portion of said main strap portion and defining an opening for reception of the free end portion of the main strap portion and said barrier member comprises a strap portion shorter than said main strap portion connected to said generally endless member, said short strap portion being of sufficient length to extend across at least a major portion of said opening of said generally endless member to provide a barrier between the generally endless member and the member to be gripped when the cinch strap is positioned in gripped encompassing relation therewith.

11. The separable fastening device according to claim 10 wherein the free end portion of the main strap portion further comprises means to grip said main strap portion and the generally endless member is in the form of a ring-like member.

12. The separable fastening device according to claim 11 wherein said means to grip said main strap portion to apply cinching forces comprises the free end portion of the main strap portion being folded upon itself and secured to itself.

13. The separable fastening device according to claim 12 wherein said retaining strap has a substantially arcuate configuration at its free end portion to facilitate gripping.

14. The separable fastening device according to claim 13 wherein said retaining strap is in the form of at least one of a hook and loop-type fastening tape having one end connected to said ringlike member and having its free end portion folded upon itself and secured thereto to provide means to grip the retaining strap while applying cinching forces at least to the main strap portion.

15. The separable fastening device according to claim 14 wherein said strap sections of said main strap portion are positioned in overlapping relation and connected by ultrasonically welded strap portions.

16. The separable fastening device according to claim 15 wherein at least said main strap portion includes yarns of an elastic material and the warp yarns extend generally along the length of the main strap portion to provide elastic properties to said strap portion in a longitudinal direction such that encompassing the member with said cinch strap and applying and maintaining cinching forces thereto, causes at least the main strap portion to become elongated from its rest condition and provides elastic restraining gripping forces about said member.

17. The separable fastening device according to claim 16 adapted for use as a tourniquet to tightly grip a human limb in encircling relation to stop or control the flow of blood therethrough and said relatively short strap portion has a free end portion having an arcuate cross-sectional configuration and is positioned and configured to extend across the opening of said ring-linke member to provide a barrier between the skin of the limb and the opening defined by the ring-like member, such that when cinching forces are applied at least to the free end portion of said main strap portion, the arcuate end portion of the relatively short strap portion slidably engages skin portions of the limb beneath the ring-like member and clusters excessive portions thereof adjacent the arcuate free end portion to thereby avoid pinching of the skin caused by excess skin portions which would otherwise be forced through the ring opening as gripping forces are applied to the limb.

18. The separable fastening device according to claim 2 wherein at least said main strap portion includes yarns of an elastic material and the warp yarns extend generally along the length of the main strap portion to provide elastic properties to said strap portion in a longitudinal direction such that encompassing the member with said cinch strap and applying and maintaining cinching forces thereto, causes at least the main strap portion to become elongated from its rest condition and provides elastic restraining gripping forces about said member.

19. An adjustable cinch strap assembly adapted to be tightly gripped about at least one member which comprises a main flexible strap portion having a first hook and loop-type fastener tape section, a surface portion of said first tape section having a plurality of flexible resilient engaging elements upstanding therefrom, a second hook and looptype fastener tape section secured in adjacent relation to the first tape section and having a surface portion of a plurality of mating flexible resilient engaging elements upstanding therefrom such that said mating engaging elements of the second tape section face in a direction opposite to the direction of the engaging elements of the first tape section, a retaining strap connected to said main strap portion at one end portion thereof and configured and dimensioned to be tightly gripped by hand, relatively rigid means to connect the retaining strap to the main strap portion, said connecting means defining an opening configured to receive the free end portion of the main strap portion, a barrier member connected to said main strap portion adjacent said connecting means and dimensioned to extend across at least a portion of said opening of said connecting means, said opposed engaging elements being so arranged that positioning said main strap portion about the member with the free end portion extending through the opening defined by said connecting means, and placing the engaging elements of the opposed strap portions in face-to-face relation and at least securely gripping said retaining strap, the application of cinching forces at least to the free end portion of said main strap portion produces encompassing gripping forces which tighten the main strap portion about at least a portion of the member and simultaneously pressing together the mating opposed surfaces of flexible resilient engaging elements causes simultaneously increasing face-to-face engagement thereof to retain the gripping forces about said member thereby applied due to the resistance to separation by said surfaces by forces parallel to the interfacial plane of engagement, and said barrier member provides a separative layer between the opening of said relatively rigid retaining means and the gripped member.

20. An adjustable cinch strap assembly adapted to be tightly gripped about at least one member which comprises a main flexible strap portion including a first tape section having a plurality of flexible resilient hooking elements of the hook and loop-type unstanding from at least one surface portion, a second tape section secured in adjacent relation to the first tape section and having a plurality of mating flexible resilient hooking elements of the hook and loop-type upstanding from an opposed surface portion such that said mating hooking elements of said second tape section face in a direction opposite to the direction of the flexible engaging elements of the first tape section, a relatively rigid retaining ring connected to said main strap portion at one end portion thereof, a retaining strap connected to said retaining ring and dimensioned and configured to be gripped by hand, means to connect the retaining ring to the main strap portion, said retaining ring defining an opening configured to receive the free end portion of the main strap portion, a barrier member connected to said main strap portion adjacent said retaining ring and dimensioned to extend across said opening of said relatively rigid retaining ring, said opposed engaging elements being so arranged that positioning said main strap portion about the member with the free end portion extending through the opening defined by said retaining means and placing the hooking elements of the opposed surfaces in face-to-face relation, the simultaneous application of generally opposed cinching forces to said retaining strap and to the free end portion of said main strap portion produces encompassing gripping forces which tighten at least the main strap portion about the member and simultaneously pressing the mating opposed surfaces of flexible resilient hooking elements together simultaneously provides progressively increasing face-to-face engagement of said surfaces to retain the encompassing gripping forces about said member and retains the main strap portion in tension due to the resistance to separation by said surface portions of mating hooking elements for forces parallel to the interfacial plane of engagement, and said barrier member provides a separative layer between the opening of said relatively rigid retaining ring and the gripped member.

21. A separable fastening device which comprises an adjustble cinch strap assembly adapted to substantially uniformly encircle a portion of a human body to constrict or control the blood flow, which comprises a main flexible strap portion having on a first surface portion a plurality of first flexible resilient hooking elements upstanding therefrom and on an opposite surface portion adjacent the first surface portion, a plurality of second complementary hooking elements such that said hooking elements of the first and second surface portions face in opposite directions, said second complementary hooking elements capable of mating with the first hooking elements when the mating opposed strap surface portions are placed in face-to-face engaged relation, a retaining strap connected to the main strap portion at one end portion and dimensioned and configured to be gripped by hand, the other end of said main strap portion being free, a relatively rigid substantially endless connecting ring securing the retaining strap to the main strap portion at one end, said connecting ring defining an opening configured to receive the opposite free end portion of the main strap portion when said main strap portion is wrapped in encircling relation with the human body portion, a barrier member connected to the main strap portion adjacent to said connecting ring and dimensioned to extend across said opening of said connecting ring, said mating hooking elements being so arranged that extending the main strap portion about the member in encircling relation therewith with the free end portion extending through the opening of the connecting ring and placing said engaging hooking elements of the opposed surface portions in face-to-face relation, the application of cinching forces to the main strap portion while gripping the retaining strap and applying forces thereto generally away from the human body portion and generally opposed to the cinching forces applied to the main strap portion, while substantially simultaneously pressing the hooking elements of the mating surfaces together to tighten the grip of the strap about the human body portion causes the main strap portion to tightly grip the human body portion while the hooking elements of the mating opposed surfaces of the strap portions become simultaneously progressively increasingly engaged in face-to-face relation to retain the gripping forces applied to the main strap portion, and said barrier member provides a separative layer between said opening of said connecting ring to prevent pinching of the layers of skin of said human body portion into said opening.

22. An adjustable separable fastening device in the form of a cinch strap assembly adapted to encircle a human limb and the like to constrict or control the blood flow therethrough which comprises a main flexible strap portion having on one section a first surface portion having a plurality of flexible resilient hook-type hooking elements upstanding therefrom and on a section connected to the first section a second surface portion opposite the first surface portion, said second surface portion having a plurality of complementary flexible resilient loop-type hooking elements such that said hooking elements of the first and second strap portion face in opposite directions, said complementary loop-type hooking elements mate with the hook-type hooking elements of the first section when the strap portions are placed in face-to-face engagement, a retaining strap connected to the main strap portion at one end portion and dimensioned and configured for gripping, the other end of said main strap portion being free, a relatively rigid generally endless ring member connecting the retaining strap to the main strap portion and defining an opening configured to receive the opposite free end portion of said main strap portion when said strap is wrapped in encircled relation to the human limb, said generally endless ring member having relatively smooth side portions to prevent snagging of said hooking elements thereagainst when the free end portion of said main strap portion is inserted into said opening, a short strap extension of said main strap portion at the ring member connection configured and positioned to extend across the ring opening to provide a protective barrier between skin portions of the limb and said ring member, said opposing hook and loop-type hooking elements being so positioned and arranged that encircling the main strap portion about the human limb with the free end portion extending through the opening of said generally endless ring member and placing the opposed hooking elements of the first and second strap portions in face-to-face relation, the application of generally opposed cinching forces to the retaining strap and to the free end portion of the main strap tighten the grip of the strap about the limb while the free end portion of said main strap extension engages and smooths excessive skin portions while accumulating such skin portions adjacent the free end portion as the grip is tightened, and simultaneously pressing the mating surfaces in fce-to-face engagement will securely adhere said mating surface portions of the main strap portion together to resist forces parallel to the interfacial plane of engagement and thereby retain the grip applied by said generally opposed cinching forces.

23. The adjustable separable fastening device according to claim 22 wherein said main flexible strap portion is comprised of two sections of hook and loop separable fastening tapes, the first section having a plurality of flexible resilient hooks upstanding therefrom, the second section having a plurality of flexible mating resilient loops upstanding therefrom, the sections further being connected at respective end portions in reversed relation to each other by an ultrasonic welded portion in a manner that the loops face in a direction opposite the direction of the hooks.

24. The adjustable separable fastening device according to claim 23 wherein said generally endless ring is a cylindrically configured metal bar configured as a substantially rectangular ring member with the end portions of said bar facing each other in close proximity therewith.

25. An adjustable separable fastening device in the form of a cinch strap assembly adapted to encircle a human limb in tightly gripped relation to control the flow of blood therethroubh which comprises a main strap constructed of nylon filamentary yarn having a first tape section of at least one of nylon hook and loop fastener tape, a second tape section having hooking elements in the form of at least one of mating nylon hooks and loops upstanding from one surface connected to the first tape section, the hooking elements of the first tape section facing in a direction opposite to the direction of the hooking elements of the second tape section, the second tape section connected in ultrasonic welded overlapping relation to the first tape section, a retaining strap connected to the main strap at one end and dimensioned and configured, to be gripped by hand the other end of the main strap being free, a relatively rigid endless ring member connecting the retaining strap to one end portion of the main strap and defining an opening configured to receive the opposite free end portion of said main strap when said main strap is wrapped in encircled relation with a limb of a human being, said generally endless ring member having relatively smooth side portions to prevent snagging of said hooking elements thereagainst when the free end of said main strap is inserted into said opening, a relatively short third tape section secured to said first tape section at the ring connection, said short third tape section having a free end portion folded upon itself and secured thereto to form an arcuate free end portion, said short third tape section being at least of a length sufficient to extend across the ring opening to provide a protective barrier between surface portions of the skin of the limb and the ring member when the cinch strap is tightened about the limb, said opposed hook and loop hooking elements being so positioned and arranged that when the main strap is encircled about the limb with the free end portion extending through the endless ring member and the opposed hook and loop hooking elements are placed in face-to-face relation, the application of cinching forces to the free end portion of the main strap while forces are applied to said retaining strap in a direction at least generally away from the limb and opposed to the cinching forces applied to the main strap portion, will place said main strap in tension while the short third tape section provides a protective barrier between the skin and the ring member and the arcuate free end portion smooths the skin and clusters excessive skin portions forwardly of said short tape section, while simultaneously pressing the hook and loop mating surfaces in face-to-face engagement will securely adhere said mating tpe sections together to resist forces parallel to the interfacial plane of engagement and thereby retains the grip applied by said generally opposed cinching forces.

26. The adjustable separable fastening device according to claim 25 wherein said retaining strap is comprised of at least one of hook and loop fastener tape.

27. The adjustable separable fastening device according to claim 26 wherein said main strap has on an outer surface portion, at least one of hook and loop hooking elements which mate with the hook and loop-type hooking elements of the retaining strap, said hooking elements being positioned such that when said main strap is cinched about a human limb, the retaining strap is securable to said surface of hooking elements.

28. An adjustable separable fastening device in the form of a cinch strap assembly adapted to encircle a human limb in tightly gripped relation to control the flow of blood therethrough which comprises a main strap constructed of filamentary yarn having a first section having at least one of hook and loop-type fastener member, a second section having at least one of mating hook and loop-type fastener member connected to the first section, the hooking elements of the first section facing in a direction opposite to the direction of the hooking elements of the second section, the second section being connected to the first section, a relatively retaining ring connected to the main strap at one end and dimensioned, to be gripped by hand, the other end of the main strap being free, said retaining ring defining an opening configured to receive the opposite free end portion of said main strap when said main strap is wrapped in encircled relation with a portion of a human body such as a limb, a relatively short section of plastic material secured to said main strap adjacent said retaining ring connection and being of a length at least sufficient to extend across at least a portion of the ring opening to provide a protective barrier between surface portions of the human body and the retaining ring when the main strap is tightened about the human body portion, said opposed hooking elements being so positioned and arranged that when the main strap is encircled about the limb with the free end portion extended through the retaining ring, the application of cinching forces to the free end portion of the main strap while applying forces to said retaining ring in a direction at least generally opposite the direction of the cinching forces will place the main strap in tension while said relatively short section of plastic material provides a protective barrier between the skin and the fastening device, and simultaneously pressing the hook and loop-type mating surfaces in face-to-face engagement will securely adhere said mating fastener members together to resist forces parallel to the interfacial plane of engagement and thereby retain the grip applied by said generally opposed cinching forces.

* * * * *

UNITED STATES PATENT AND TRADEMARK OFFICE
CERTIFICATE OF CORRECTION

PATENT NO. : 4,149,540           Page 1 of 3

DATED : April 17, 1979

INVENTOR(S) : Russell Hasslinger

It is certified that error appears in the above—identified patent and that said Letters Patent are hereby corrected as shown below:

Column 4, line 31, "Futther" should read --Further--

Column 4, line 38 "srap" should read --strap--

Column 4, line 39 "beelastic" should read --be elastic--

Column 4, line 57 "elatic" should read --elastic--

Column 5, line 24 "he" should read --the--

Column 5, line 56 "cich" should read --cinch--

Column 5, line 57 "cicnching" should read --cinching--

Column 5, line 62 "ro" should read --to--

Column 6, lines 6 and 7 "alternae" should read -- alternate--

Column 7, line 37 "lowr" should read --lower--

UNITED STATES PATENT AND TRADEMARK OFFICE
CERTIFICATE OF CORRECTION

PATENT NO. : 4,149,540        Page 2 of 3
DATED : April 17, 1979
INVENTOR(S) : Russell Hasslinger It is certified that error appears in the above-identified patent and that said Letters Patent are hereby corrected as shown below:

Column 9, line 42 "us" should read --use--

Column 10, line 31 "scrubbing" should read --securing--

Column 12, line 46 "ring-linke" should read --ring-like--

Column 13, line 7 "looptype" should read --loop-type--

Column 13, line 47 "unstanding" should read --upstanding--

Column 14, line 14 "for" should read --by--

Column 14, line 19 "adjustble" should read --adjustable--

Column 15, line 45 "fce-to-face" should read --face-to-face--

Column 16, line 2 "therethroubh" should read --therethrough--

UNITED STATES PATENT AND TRADEMARK OFFICE
CERTIFICATE OF CORRECTION

PATENT NO. : 4,149,540

DATED : April 17, 1979

INVENTOR(S) : Russell Hasslinger

It is certified that error appears in the above-identified patent and that said Letters Patent are hereby corrected as shown below:

Column 16, line 50 "tpe" should read --tape--

Column 17, line 8 before "retaining" insert --rigid--

Signed and Sealed this

Twenty-fifth Day of December 1979

[SEAL]

*Attest:*

*Attesting Officer*

SIDNEY A. DIAMOND

*Commissioner of Patents and Trademarks*